(12) United States Patent
Fislage et al.

(10) Patent No.: US 9,149,770 B2
(45) Date of Patent: Oct. 6, 2015

(54) HOLLOW FIBER CAPILLARY MEMBRANE AND METHOD FOR THE PRODUCTION THEREOF

(75) Inventors: Rainer Fislage, St. Wendel (DE); Klaus Heilmann, St. Wendel (DE); Torsten Keller, Hermeskeil (DE); Holger Lichau, Mücke/Ober-Ohmen (DE); Igor Raiko, St. Wendel (DE); Roland Sander, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 559 days.

(21) Appl. No.: 12/594,694

(22) PCT Filed: Apr. 21, 2008

(86) PCT No.: PCT/EP2008/003195
§ 371 (c)(1),
(2), (4) Date: Oct. 5, 2009

(87) PCT Pub. No.: WO2008/128749
PCT Pub. Date: Oct. 30, 2008

(65) Prior Publication Data
US 2010/0163488 A1 Jul. 1, 2010
US 2010/0326915 A2 Dec. 30, 2010

(30) Foreign Application Priority Data

Apr. 23, 2007 (DE) .................. 10 2007 0129 051

(51) Int. Cl.
*B01D 61/00* (2006.01)
*B01D 39/00* (2006.01)
(Continued)

(52) U.S. Cl.
CPC ............ *B01D 69/088* (2013.01); *B01D 61/027* (2013.01); *B01D 61/145* (2013.01);
(Continued)

(58) Field of Classification Search
CPC ........ B01D 71/68; B01D 69/08; B01D 69/10; B01D 2323/42; B01D 2323/02; B01D 61/025; B01D 67/0093; B01D 2325/36; B01D 71/28; B01D 2323/06; B01D 2323/12; C02F 1/444
USPC ............ 210/500.23, 500.41, 500.42, 500.36; 264/178.1, 177.14, 177.16
See application file for complete search history.

(56) References Cited

U.S. PATENT DOCUMENTS 4,933,085 A * 6/1990 Kneifel et al. ........... 210/500.39
5,034,129 A * 7/1991 Ten Hove .................. 210/490
(Continued)

FOREIGN PATENT DOCUMENTS

DE 690 09 435 T2 9/1994
DE 19907824 A1 8/2000
(Continued)

OTHER PUBLICATIONS

Marcel Mulder; Basic Principles of Membrane Technology; $2^{nd}$ edition; 1996; pp. 71-91; Kluwer Academic Publishers; Great Britain.
(Continued)

*Primary Examiner* — Ana Fortuna
(74) *Attorney, Agent, or Firm* — Millen, White, Zelano, Branigan, P.C.

(57) ABSTRACT

A hollow fiber membrane made of two coextruded layers A and B, wherein layer B has a non-woven type structure having a mesh size of 0.1 to 10 μm and layer A has a porous structure. A method for producing a membrane according to the invention and the use thereof is also disclosed.

33 Claims, 3 Drawing Sheets

(51) Int. Cl.

| | |
|---|---|
| *B01D 11/00* | (2006.01) |
| *B01D 39/14* | (2006.01) |
| *B01D 67/00* | (2006.01) |
| *B01D 63/02* | (2006.01) |
| *B01D 69/08* | (2006.01) |
| *B01D 61/02* | (2006.01) |
| *B01D 61/14* | (2006.01) |
| *B01D 69/02* | (2006.01) |
| *B01D 69/12* | (2006.01) |
| *B01D 71/44* | (2006.01) |
| *B01D 71/68* | (2006.01) |
| *A61M 1/16* | (2006.01) |

(52) U.S. Cl.
CPC ............... *B01D 69/02* (2013.01); *B01D 69/12* (2013.01); *B01D 71/44* (2013.01); *B01D 71/68* (2013.01); *A61M 1/16* (2013.01); *B01D 2325/02* (2013.01)

(56) References Cited

U.S. PATENT DOCUMENTS

| | | | |
|---|---|---|---|
| 5,141,642 A | 8/1992 | Kusuki et al. | |
| 5,145,583 A | 9/1992 | Angleraud et al. | |
| 5,383,925 A * | 1/1995 | Schmitt | 623/1.53 |
| 5,468,430 A * | 11/1995 | Ekiner et al. | 264/28 |
| 5,472,607 A | 12/1995 | Mailvaganam et al. | |
| 5,863,645 A | 1/1999 | Misoo et al. | |
| 5,868,936 A | 2/1999 | Ofsthun et al. | |
| 5,871,649 A | 2/1999 | Ofsthun et al. | |
| 5,919,370 A | 7/1999 | Rottger et al. | |
| 6,074,718 A * | 6/2000 | Puglia et al. | 428/36.5 |
| 6,146,747 A * | 11/2000 | Wang et al. | 428/310.5 |
| 6,284,137 B1 * | 9/2001 | Hajikano et al. | 210/500.41 |
| 6,565,782 B1 | 5/2003 | Wang et al. | |
| 6,809,971 B2 * | 10/2004 | Terzioglu et al. | 365/194 |
| 6,951,811 B2 * | 10/2005 | Sorimachi | 438/637 |
| 7,087,168 B2 * | 8/2006 | Oishi et al. | 210/500.23 |
| 7,128,861 B2 * | 10/2006 | Hamanaka et al. | 264/171.26 |
| 7,172,075 B1 | 2/2007 | Ji | |
| 7,306,754 B2 | 12/2007 | Krause et al. | |
| 7,632,439 B2 | 12/2009 | Mullette et al. | 264/41 |
| 7,815,987 B2 * | 10/2010 | Mickols et al. | 428/36.5 |
| 7,861,869 B2 * | 1/2011 | Beckers et al. | 210/490 |
| 2004/0124135 A1 * | 7/2004 | Sale et al. | 210/483 |
| 2005/0274665 A1 | 12/2005 | Heilmann et al. | |
| 2007/0199891 A1 * | 8/2007 | Mabuchi et al. | 210/500.23 |
| 2009/0216173 A1 | 8/2009 | Gensrich et al. | |

FOREIGN PATENT DOCUMENTS

| | | |
|---|---|---|
| DE | 100 33 401 A1 | 1/2002 |
| DE | 10 211 051 A1 | 10/2003 |
| DE | 697 21 223 T2 | 2/2004 |
| DE | 10 2004 023 410 A1 | 12/2005 |
| EP | 1547628 A1 | 6/2005 |
| JP | 62019205 A * | 1/1987 |
| WO | WO 96/37282 | 11/1996 |

OTHER PUBLICATIONS

W. Samtleben and M. J. Lysaght; Dialysis Techniques: Therapeutic Plasma Exchange and Related Techniques; Replacement of Renal Function by Dialysis; 5$^{th}$ edition; 2004, pp. 709-724; Kluwer Academic Publishers; Great Britain.

* cited by examiner

HOLLOW FIBER CAPILLARY MEMBRANE AND METHOD FOR THE PRODUCTION THEREOF

This is a U.S. National Phase application of PCT application number PCT/EP2008/003195, filed Apr. 21, 2008 which claims priority benefit of DE 10 2007 0129 051.6 filed Apr. 23, 2007, each of which is incorporated herein by reference in its entirety.

FIELD OF THE INVENTION

The present invention relates to a hollow fibre capillary membrane and a method for the production thereof plus its use in particular in plasmapheresis.

BACKGROUND OF THE INVENTION

Capillary membranes of different compositions are known in particular because of their increasing use in dialysis or also in plasmapheresis. The use and the production of membranes, in particular of capillary membranes, in dialysis is described for example in the publication by Samtleben and Lysaght in: Hörl et al. Replacement of Renal Function by Dialysis 5th ed., Kluwer, 2004, pp. 709 to 724.

Thus WO 96/37282 describes a membrane, in particular for haemodialysis, which has a separating layer with a cut-off between 500 and 5000000 dalton, a supporting layer and a layer co-determining the hydraulic permeability, wherein the separation limit and hydraulic permeability are set mutually independently. However, it is very expensive to build up the membrane with different pore sizes within the individual layers.

EP 1547628 A1 describes plasma purification membranes and a plasma purification system, and in particular is geared towards specific physical properties, in particular the breaking resistance of the membrane due to the high stress load during plasma purification. This involves in particular protein and immunoglobulin permeability. In the membrane with a sponge-like structure, a gradient of the pore size is set, wherein a larger pore size is to be found on the outer surface than on the inner surface of the membrane.

U.S. Pat. No. 6,565,782 relates to synthetic polymeric microfiltration membrane materials with high surface porosity which can be obtained by co-casting a sulfone polymer with a hydrophilic polymer, such as polyvinylpyrrolidone. Disadvantages occur with this membrane in particular in relation to the separation of cellular components of the blood from the plasma phase, since the pressure on the blood cells caused by the use of small-pored membranes can lead to damage to the blood cells.

So-called hollow fibre spinnerets are used in most cases to produce such capillary membranes. An overview of this and other techniques for the production of hollow fibre membranes is disclosed in M. Mulder, Basic Principles of Membrane Technology second ed., Kluwer 1996, pp. 71-91.

When a hollow fibre membrane is produced by means of a hollow fibre spinneret, the hollow fibre membrane is produced in a so-called precipitation spinning process, wherein the polymers to be precipitated emerge from an annular slit of a spinneret arrangement, while the corresponding precipitant flows out of a central precipitant bore.

A hollow fibre spinneret of the named type is disclosed for example in DE 10211051 A1.

SUMMARY OF THE INVENTION

Typical plasmapheresis filters of the state of the art contain in most cases hydrophobic membranes, for example of polypropylene, polysulfone, etc.

Since these hydrophobic membranes cannot be wetted with water, the filters containing these membranes are typically made hydrophilic with water under pressure. For the subsequent blood treatment, it is therefore ensured that all the air inclusions inside the pores have been expelled and therefore do not enter the blood circulation. Disadvantageously, these filter modules with hydrophobic hollow fibre membranes must be delivered filled with water to the clients and patients. Attempts are being made to circumvent the raw material and distribution costs and the difficulty of guaranteeing the sterility of such filled modules.

Problems with the plasma membranes known until now are their low permeability for large lipoproteins and pressure-induced damage to blood cells due to the transmembrane pressure difference, i.e. due to the negative pressures acting on a blood cell adhering to the membrane wall and adjacent to a pore opening. The lower the pore size is, the greater, with a given transmembrane pressure difference (TMP), the pressure difference acting on a blood cell that is large relative to the pore size is on the affected section of the blood cell. In such cases, it has often been shown that the pressure acting on the corresponding section of the blood cell is so great that the blood cell walls burst, leading to haemolysis. Attempts are therefore being made to produce as high as possible a porosity on the blood-side membrane wall surface, with the result that the negative pressure impact on the blood cell wall is distributed over a larger surface area of the blood cell.

Because of the low permeability for large lipoproteins of the membranes known from the state of the art, difficulties arise with these in particular during the filtration of lipaemic blood due to the drop in the screening coefficients. Hydrophobic plasma membranes often display, in blood treatment, the negative property of clogging in the course of the treatment due to interaction with the nonpolar blood lipids. A drop in the screening coefficient is therefore often observed during the blood treatment.

It was therefore an object of the present invention to provide a hollow fibre membrane which in particular makes possible a gentle plasmapheresis, in particular a gentle plasma filtration of blood. Furthermore, such a hollow fibre membrane should also have, in addition to the largest possible openings for a good lipoprotein permeability with a simultaneously high selectivity, a high porosity for an improved blood compatibility.

According to aspects of the invention, this object is achieved by an integral hollow fibre membrane, consisting of two co-extruded layers A and B, wherein layer B has a non-woven type structure with a mesh size of 0.1 to 10 μm and layer A has a porous structure. By "mesh size" is meant in this connection the greatest distance, in a non-woven type or net-like structure, between the individual branchings of the structure forming the non-woven material or net. The thickness of the webs of the branching is 0.1-0.5 μm in this case.

Layer B preferably forms the so-called blood-contact side and layer A the filtrate side of the hollow fibre membrane, for example in a blood treatment in which the blood is passed through the inside of the hollow fibre.

As a rule, the blood-contact side is the inner layer of the hollow fibre membrane and layer A, thus the filtrate side, is the outer layer of the membrane. In less preferred embodiments, however, it is also possible for layer B to be the outer layer (the blood-contact side) and layer A the inner layer (filtrate side).

Because of the membrane according to aspects of the invention and in particular the presence of the non-woven type inner layer B, a lower negative pressure acts on a section of a blood cell through the transmembrane pressure difference than in the case of a small-pored membrane of the state of the art, with the result that in particular the cellular components of the blood can be separated particularly gently from the plasma phase of the blood.

It is preferred that layer A consists of at least three successive zones A1, A2, A3 of different porosity, wherein zone A1 forms the surface of layer A and has pores with an average pore size of 0.7 to 2 μm. The thickness of zone A1 typically lies in the range of 9 to 11 μm, and is preferably 10 μm, with a preferred wall thickness of approx. 60 μm.

Adjoining this is zone A2 which is arranged between zones A1 and A3 and has an average pore size of more than 200 nm.

The thickness of this zone A2 is typically approx. 10 μm, with a preferred total wall thickness of 60 μm. In general, the thickness of zone A2 is thus approximately ⅙ of the total wall thickness.

A third zone A3 is directly adjacent to layer B and is typically positively connected to the non-woven type structure of layer B. Zone A3 has a pore-size gradient towards layer B, i.e. the pore size increases towards layer B. The thickness of zone A3 is approx. 30 μm for a total wall thickness of 60 μm. In general, the thickness of zone A3 is thus approx. 50% of the total wall thickness.

The layer thicknesses of zones A1, A2, A3 are designed in relation to the total wall thickness. An increase of the total wall thickness by e.g. 100% will also increase the layer thickness of the individual zones by approx. 100%, wherein the relationships of the layer thicknesses to one another remain constant. In the transition to even greater layer thicknesses of the total wall thickness, however, it was established during production that the relationships of the layers to one another alter, in particular the layer thickness of layer A2 turns out to be relatively less than in the case of thinner-walled membranes.

Important for the capillary membrane according to aspects of the invention consisting of two co-extruded layers A and B is, as already stated above, the different pore size or mesh size in layers A and B, wherein the mesh size of the meshes in layer B is not only larger relative to the pore size of the above-mentioned outermost zone of layer A of zone A1, but also relative to all the pores of the whole of layer A.

The two layers A and B perform different functions according to aspects of the invention:

Because of its greater mass density, the outer layer A gives the hollow fibre membrane according aspects of to the invention its mechanical stability, in particular also when producing the membrane using the method according to aspects of the invention, which is described in detail below. Furthermore, this layer has the zone with the smallest average pore diameter (greater than 200 nm) in the whole membrane and is therefore the layer that determines selection with regard to filtration. The function of layer A is therefore to give the membrane according to aspects of the invention stability and selectivity.

The layer B, preferably arranged on the inside, i.e. the layer facing the blood or another bodily fluid, has in its net-like structure a mesh size that is much greater than the pore size of layer A. Not least because of its net-like or non-woven type structure and the resultant low mass density, this layer has almost no mechanical strength and must therefore be supported by the additional layer A. Layer B has the task in the blood treatment process of merely holding back the cellular components of the fluid to be passed through it.

Because of the non-woven type structure of this layer, it was surprisingly shown that this takes place in an unexpectedly gentle manner vis-à-vis the cells. This layer therefore essentially has the function of compatibilizing the fluid to be filtered and the membrane with each other.

The non-woven type structure and the concomitant high porosity of layer B further result, surprisingly, in an improved screening coefficient which is constant over the course of the treatment for high-molecular-weight components of blood, such as e.g. triglycerides or lipoproteins. It was shown that the screening coefficients remain essentially constant over a longer course of treatment, unlike plasma membranes known until now. Thus it is established in the case of plasma membranes known until now that the pores of the inner surface can be clogged by large blood lipid particles present in the blood. As a result, it is observed that the screening coefficients drop, since there is a smaller total flow-through passage through the membrane wall and the effective permeability drops. On the other hand, the porosity of the membrane according to aspects of the invention is so great on the blood-contact side that there are enough fluid passages, even by adsorption of the large blood lipid particles, to maintain the desired permeability.

In order to give the membrane the optimum properties as regards stability and selectivity, the ratio of the layer thicknesses of layer A to layer B is 4:1 to 6:1, with the result that layer A in particular can perform its supportive stability function particularly well.

It was shown that an internal diameter of 280 to 400 μm is advantageous for the planned use, in order to withstand even more pronounced pressures and pressure differences. Typical total wall thicknesses of the hollow fibre membranes according to aspects of the invention are 40 to 80 μm, quite particularly preferably 60 μm. Such membranes according to aspects of the invention are typically used in fibre bundle sizes of 1300 to 2600 fibres for the production of plasma filters with membrane surfaces of 0.3 and 0.6 $m^2$.

The membrane surface also determines the physical parameters of the membrane: a plasma filter with a bundle consisting of a large number of hollow fibre membranes according to aspects of the invention ("hollow fibre bundle") with a total membrane surface of 0.3 $m^2$ is provided for use with blood flows of 100 ml per minute and filtrate flows of up to 30 ml/m, the plasma filter with a membrane surface of 0.6 $m^2$ for blood flows of 200 ml per minute and filtrate flows of up to 3 ml/min.

Each layer consists of a polymer mixture of at least two polymers selected from polysulfone (PSU), polyvinylpyrrolidone (PVP), polyethersulfone (PES), polyetherimide (PEI), polyamide (PA), polycarbonate (PC), polystyrene (PS), polymethyl methacrylate (PMMA), polyvinylidene fluoride (PVDF), polyacrylonitrile (PAN), polyimide (PI) and/or polyurethane (PU).

A combination of polysulfone and polyvinylpyrrolidone is quite particularly preferred.

The concentration of both components in the different layers can be set independently of each other in accordance with what is required of the membrane structure. A high polymer concentration for the outer layer results in high viscosities in the not yet precipitated out membrane, and thus in particular a low porosity, and a low polymer concentration for the inner layer B results in highly porous non-woven type membrane structures.

An object of the present invention is also achieved by a method for the production of a hollow fibre membrane according to aspects of the invention, comprising the steps of
  (a) preparing two spinning mass solutions A and B, wherein the viscosity of spinning mass solution A is higher than the viscosity of spinning mass solution B,
  (b) setting the precipitation bath temperature at more than 70° C., (c) bringing the two spinning mass solutions A and B into contact with an internal precipitant through a hollow fibre spinneret, (d) precipitating the hollow fibre membrane.

The setting of the precipitation temperature at more than 70° C., in particular more than 75° C., makes possible a higher degree of moisture in the area around the precipitation slit, with the result that pores with a small diameter form on the outside of the membrane, in particular in the outermost layer described according to aspects of the invention.

The viscosity of the spinning masses is thus also set depending on the proportion of the individual components. This is dependent on the molecular weight of the individual components.

The viscosity of the spinning mass solution A is 7000 to 18000 mPa·s, in particular 9000 to 14000 mPa·s, depending on the desired membrane structure. The spinning mass solution A typically contains 15 to 25% polysulfone (PSU), 4 to 8% polyvinylpyrrolidone (PVP) and 81-67% solvent (98-100% DMAC and 0-2% water). 17.5-22.5% PSU, 5-8% PVP is preferred, the remainder being solvent (80-100% DMAC and 0-20% water). 19-21% PSU, 5.5-7% PVP is quite particularly preferred, the remainder being solvent (98-100% DMAC, 2-0% water). Unless otherwise indicated, the percentages always refer to wt.-%.

The viscosity was determined by means of a rotating viscometer (Haake VT 550) which was temperature-controlled at 40° by means of the following instructions:

In the viscosity measurement, the test substance was located in the annular slit between concentrically arranged cylinders, the "rotating body" and "measuring cup". The rotational speed was preset and the effective force (shear stress) measured. The temperature-control vessel and the rotating body MV-DIN were first screwed to the basic structure. The zero point was then checked and set. The torque motor was switched off and the torque display set to zero with the button provided for the purpose. For the actual measurement, the measuring cup was filled up to the corresponding fill mark with the air-bubble-free test solution and fixed in the temperature-control vessel with the locking screw connection. The rotational speed stage was then preset. The programme was set and the viscosity read after the expiry of the measuring time.

The rotational speed stage 3 was selected on the device for the measurement. The measurement lasted 30 min. The viscosity value was read after the pre-setting of the programme set in the apparatus. The programme S1 was selected for measurements in manual mode.

The viscosity of spinning mass solution B is preferably less than 1000 mPa·s and it contains 5 to 15% polysulfone, 4 to 8% polyvinylpyrrolidone and 91-77% solvent (100% DMAC). 7-13% PSU, 4-7% PVP is preferred, the remainder being solvent (100% DMAC). 8-12% PSU, 5-7% PVP is quite particularly preferred, the remainder being solvent (100% DMAC).

The finished membrane contains approx. 3% PVP after the rinsing and drying steps. This PVP is bound and only minimally elutable.

Important in this connection, as shown above, is the different viscosity of the two spinning mass solutions A and B, resulting in the different porosity in the two co-extruded layers A and B of the hollow fibre membrane according to aspects of the invention.

In relation to the viscosity of the spinning mass solution B, care must also be taken that the viscosity is not too low, typically not less than 300 mPa·s, since otherwise the so-called beading phenomenon, which represents a preliminary stage to dripping, will occur. In this case the precipitant no longer flows uniformly, whereby the internal diameter changes in rapid succession, with the result that the hollow fibre takes on the appearance of a string of beads. This occurs in particular when the spinning mass solution B has a viscosity of less than 300, in particular less than 200, mPa·s and is precipitated softly. In this connection, "precipitated softly" means that there is a large proportion of solvent in the precipitant of the precipitation or coagulation bath, resulting in a slow coagulation of the polymer thread and leading to larger pores.

Within the framework of the invention, the size of the membrane, i.e. also the wall thickness and the internal diameter, can be varied within relatively wide ranges, whereby it is possible to adapt the membrane to different intended uses. For haemodialysis, haemodiafiltration and haemofiltration, and also in plasmapheresis, the wall thickness is typically 10 to 70 μm and in the ultrafiltration application the wall thickness can be some 100s μm, e.g. 1000 μm, wherein the dimensions can be increased or decreased by a person skilled in the art.

During precipitation with a precipitant, e.g. a mixture of dimethylacetamide (DMAC) and water, for example 70% DMAC and 30% water, preferably 80% DMAC and 20% water, the desired non-woven type, large-pored structure of layer B according to aspects of the invention forms using the method according to aspects of the invention.

The precipitation rate is also particularly important; it is set by the spinning speed of 200 to 400 mm per second, quite particularly preferably 200 to 250 mm per second, and also by a precipitation slit height of 5 to 50 mm.

In order to produce the necessary large pores in layer B, the spinning mass must be precipitated slowly, with the result that the resultant hollow fibre membrane remains very soft and mechanically unstable in the precipitation slit.

In the range of the spinning speed set according to aspects of the invention, the soft precipitant cannot pass through the whole membrane wall and the membrane enters the precipitation bath (or coagulation bath), without pores already having formed on the outside. The formation of the pores on the outside is, as already explained above, initiated by as high as possible a degree of moisture in the area around the precipitation slit which is set by the temperature of the precipitation bath. After emerging from the extrusion die, the polymer fibre is preferably guided in an enclosure (e.g. a pipe or the like) as far as the surface of the precipitation bath. The degree of moisture can be regulated in the enclosure.

The membrane obtained according to aspects of the invention still contains large quantities of extractable free polyvinylpyrrolidone in a quantity of approx. 1 g/m². This is rinsed out with a solvent, such as e.g. water, in a rinsing bath.

The temperature of the rinsing bath is typically kept in the range of 60 to 80° C. The membrane must, as far as possible, be freed of polyvinylpyrrolidone, since otherwise elutable PVP can enter the blood circulation. This can preferably also be avoided through drying temperatures of the membrane obtained according to aspects of the invention in the range of 80 to 110, in particular 90 to 100° C.

Other subjects of the present invention are the use of the hollow fibre membrane according to aspects of the invention for separation processes in the nanofiltration and ultrafiltration ranges, in particular for haemodialysis and haemodiafiltration and haemofiltration.

The two-component membranes according to aspects of the invention have good mechanical properties, such as strength, high breaking elongation in the dry state. The membranes can be housed dry in the filter module and dispatched dry. The fact that filter modules equipped with the hollow fibre according to aspects of the invention can be wetted directly by blood is particularly important for the blood treatment application method.

BRIEF DESCRIPTION OF THE DRAWINGS

The invention is explained in more detail by means of the figures and an embodiment example, but these are not to be considered limiting.

There are shown in

DETAILED DESCRIPTION OF AN EXEMPLARY EMBODIMENT OF THE INVENTION

A hollow fibre membrane according to an exemplary embodiment of the invention was prepared, wherein the spinning mass solution A consisted of 20% polysulfone (Solvay, UDEL P-3500 LCD), 6% polyvinylpyrrolidone (ISP, PVP K-90) and 1% water, the remainder being dimethylacetamide, and the spinning mass solution B for the inner layer B consisted of 10 wt.-% polysulfone, 5.5% polyvinylpyrrolidone, the remainder being dimethylacetamide.

The precipitant consisted of 80% dimethylacetamide and 20% water.

A spinning nozzle according to DE 10211051, incorporated in a spinning block, was used as spinning nozzle.

The spinning block temperature was set to 60° C. The precipitation slit height was 30 mm and the spinning speed 250 mm per second.

The temperature of the precipitation bath was approx. 80° C.

After precipitation and drying, the thus-obtained hollow fibre membrane according to the exemplary embodiment of the invention was examined by means of REM photographs.

The REM photographs were produced by means of a scanning electron microscope customary in the trade.

Figure 1:
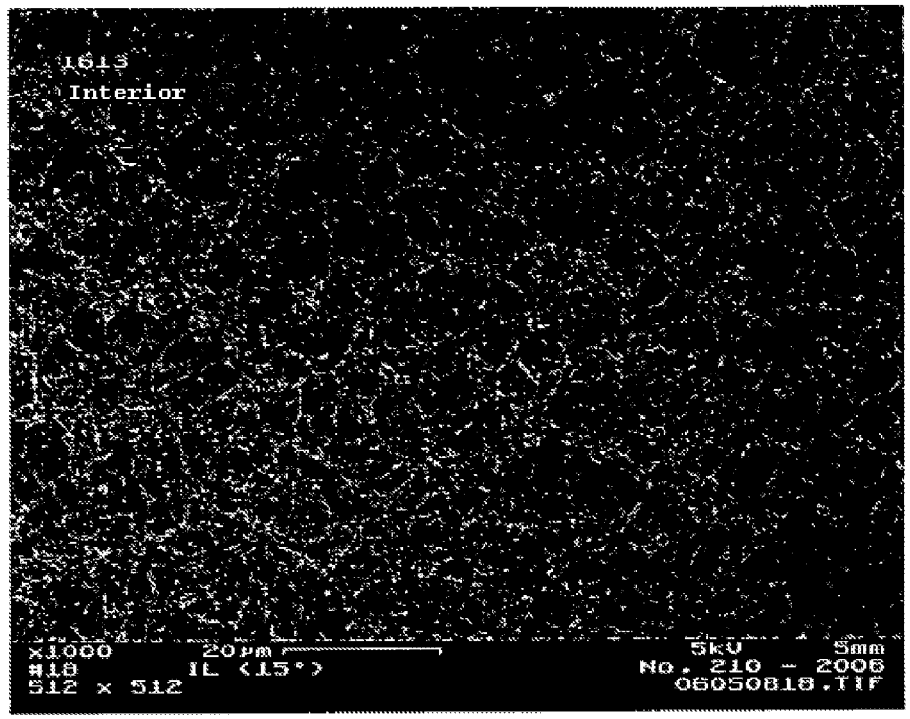
FIG. 1: an REM photograph of layer B of an exemplary embodiment of the invention magnified 1000×.
Figure 2:
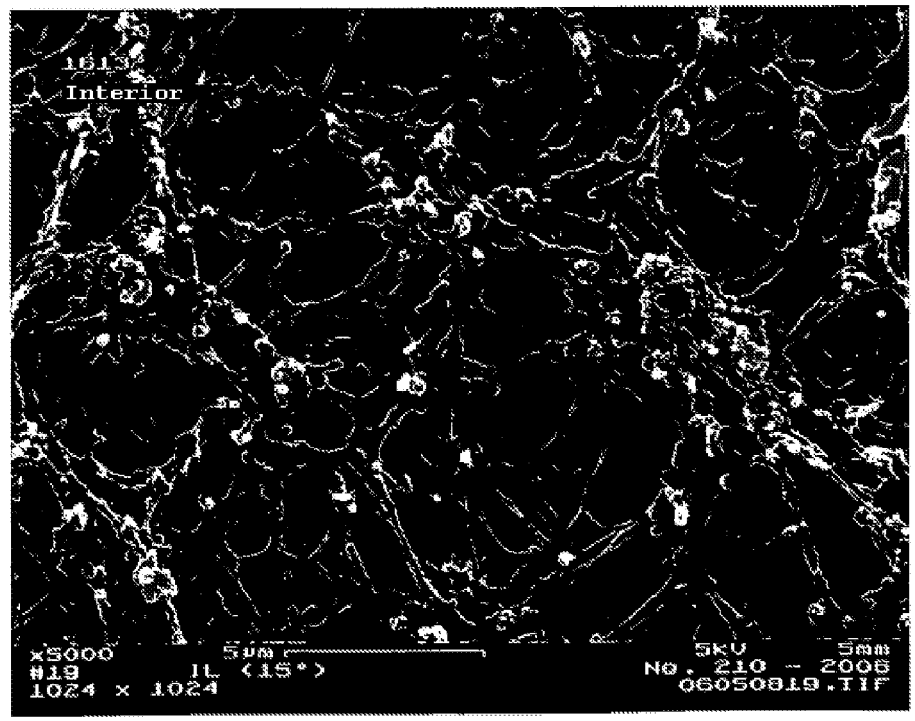
FIG. 2: an REM photograph of layer B of an exemplary embodiment of the invention magnified 5000×.

FIGS. 1 and 2 show REM photographs magnified 1000× (FIG. 1) and 5000× (FIG. 2) of layer B, in other words of the inside of the hollow fibre membrane according to the exemplary embodiment of the invention.

Both photographs show the non-woven type structure of layer B which is built up from many net-like struts (webs). This non-woven type structure is not a typical porous structure in the conventional sense, such as is present in layer A for example.

Figure 3:
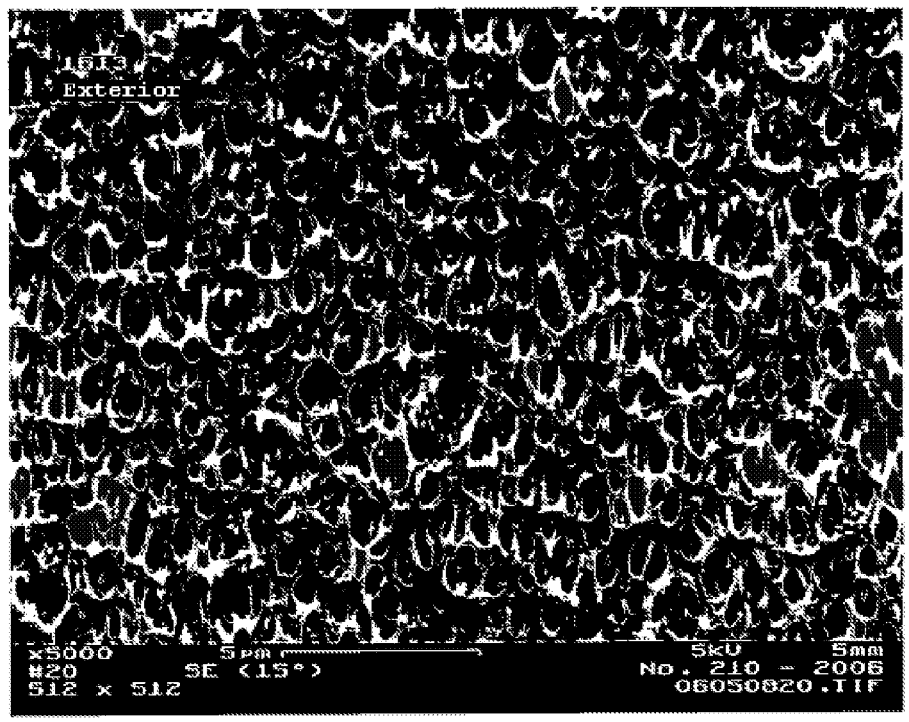
FIG. 3: an REM photograph of layer A of a hollow fibre membrane according to an exemplary embodiment of the invention.

FIG. 3 shows an REM photograph magnified 5000× of the outside of the hollow fibre membrane according to the exemplary embodiment of the invention (layer A) with an average pore size of approx. 1 μm as a result of the high moisture content in the precipitation slit during precipitation. Overall, a very high pore density can be seen with a small portion of matrix material.

Figure 4:
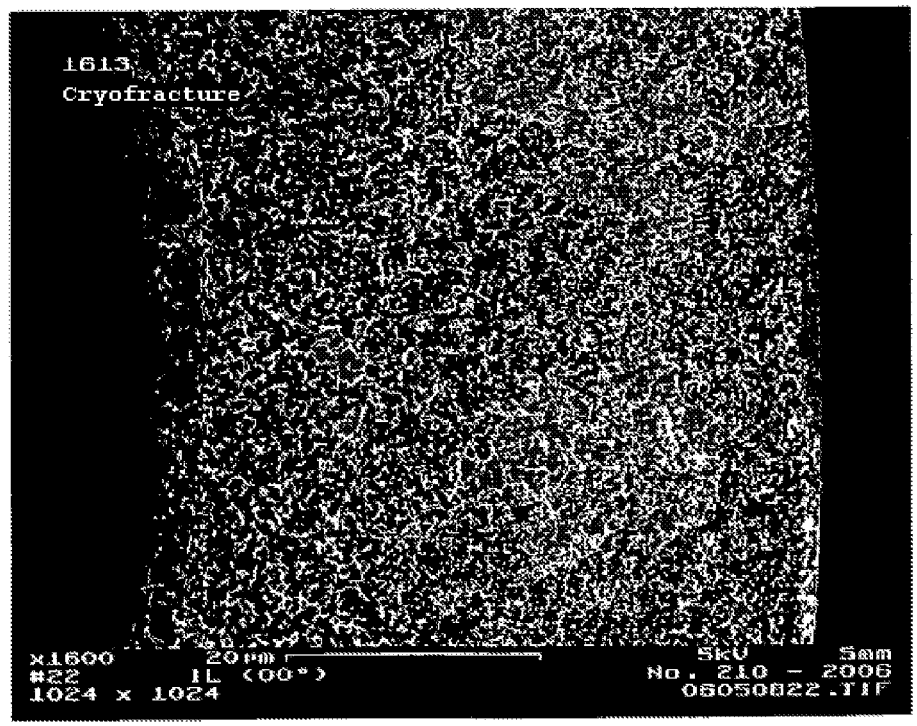
FIG. 4: an REM photograph of the cross-section through a hollow fibre membrane according to an exemplary embodiment of the invention.

In FIG. 4, an REM photograph magnified 1600× of the cross-section through a hollow fibre membrane according to the exemplary embodiment of the invention which has been exposed by so-called "cryofracture" is shown. "Cryofracture" means that the hollow fibre membrane according to the invention is immersed in liquid nitrogen and then broken manually in the lateral direction.

The two-layered structure of the membrane according to the exemplary embodiment of the invention can be seen from FIG. 4 wherein, because of the zonal structure of layer A, a clear boundary line between the two layers A and B is not very markedly pronounced, but both pass gradually into each other via the gradients obtained according to the exemplary embodiment of the invention in the individual zones of layer A.

The ultrafiltration rate, the screening coefficients and the permeability were also measured.

Figure 5:
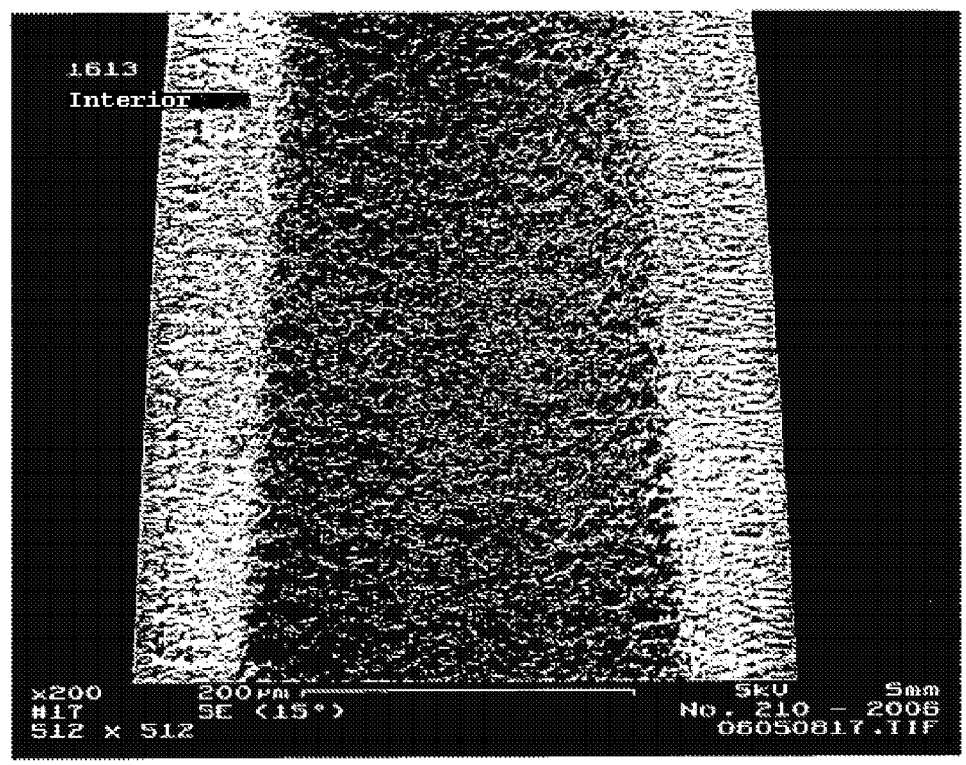
FIG. 5: an REM photograph of a longitudinal section through a hollow fibre membrane according to an exemplary embodiment of the invention.

In FIG. 5, an REM photograph magnified 200× of the longitudinal section through a hollow fibre membrane according to the exemplary embodiment of the invention is shown.

The longitudinal section is obtained by cutting through the hollow fibre according to the exemplary embodiment of the invention in longitudinal direction with a suitable cutting device, for example a so-called microtome knife.

In the figure, the irregular structures in the hollow fibre membrane wall stem from the cutting channels of the microtome knife.

The non-woven type network structure of the inside of the hollow fibre membrane according to the exemplary embodiment of the invention can be readily recognized in FIG. 5.

Ultrafiltration Rate

The aqueous ultrafiltration rate of the hollow fibre membrane according to the exemplary embodiment of the invention was determined using the following equation $$UF = V_{filtrate} \times 3600)/t \times ((\rho_{in} + \rho_{out})/2) \times 0.75)$$

by means of a dialysis tube system known from the state of the art, wherein UF represents the ultrafiltration rate in (ml/(h× mm Hg), $V_{filtrate}$ the filtrate volume in ml (in the present case: 1000 ml), t the time in seconds (to filter 1000 ml), $\rho_{in}$ the pressure of the blood-side intake (mbar) and $\rho_{out}$ the pressure of the blood-side run-out (mbar) at the device.

The blood outlet (blood-side run-out) was closed during the measurement, with the result that only filtration occurred.

An ultrafiltration value (UF value) in the range of 4500 to 5000 ml/h×mmHg×m² was measured for the membranes according to the exemplary embodiment of the invention (surface area 0.6 m²).

Screening Coefficient 1000 ml lipaemic whole blood with a triglyceride content of 200-300 mg/dl was used for a module with a surface area of 0.6 m². This blood is circulated through the lumen of the fibre for one hour at a blood flow of 200 ml/min. During this time, a filtrate flow of 60 ml/min is simultaneously filtered to the outside through the fibre wall. The screening coefficient for LDLs (low-density lipoproteins) under these conditions is at least 90%, typically 95-100%, mostly 99%. The screening coefficient for LDLs remains constant over a period of time corresponding to at least the period of time for the blood treatment of a common plasma filtration.

Free Polyvinylpyrrolidone Content

The polyvinylpyrrolidone residue from the membrane according to the exemplary embodiment of the invention according to an extract from the end-product was <1 mg. The last value is therefore advantageous in particular because the hollow fibre membrane according to aspects of the invention is thus used in particular in dialysis treatments which are carried out over very long periods of time. In particular, the membrane according to aspects of the invention can be used for membrane pheresis treatments, where limit values of up to 5 mg release polyvinylpyrrolidone per filter with 0.6-m² membrane surface determined using the method below are reasonable. The membrane according to one or more aspects of the invention lies well below this limit value.

Residues other than polyvinylpyrrolidone were not able to be discovered in the extract from the filter.

The polyvinylpyrrolidone was extracted according to the following instructions:

Two plasma filters from the same batch were used in the extraction.

Sample no. 1 consisted of a fibre bundle (total membrane surface 0.6 m²), as did sample 2. Each plasma filter was extracted with 1000 ml water at 37° Celsius recirculating over 90 minutes.

The flow at the blood-side inlet of the plasma filter was 200 ml. 60 ml/min. thereof was filtered and 140 ml/min. flowed back out of the filter at the blood-side outlet.

Both the water at the blood-side outlet and the filtrate were returned to the solvent reservoir.

At the used volume of 1000 ml water, the measured values in mg/l also corresponded to the values for mg/filter.

The results are shown in Table 1.

TABLE 1

Analysis values of hollow fibre membranes according to an exemplary embodiments of the invention

| Parameter | Measurement method | Unit | Sample no. 2600-S-0847-1 | Sample no. 2600-S-0847-2 |
|---|---|---|---|---|
| PVP | quantitative IR | mg/filter | 0.86 | 0.90 |
| GC-volatile substances (as cyclohexanol) | GC-MSD | mg/l | <0.10 | <0.10 |

The concentration of polyvinylpyrrolidone was determined by means of quantitative IR spectroscopy and had a value of 0.86 to 0.90 mg/filter. For the evaluation, the CO oscillation band in the wave number range of 1630-1735 cm$^{-1}$ was used.

As can be seen from Table 1, the values for elutable PVP in both samples are thus less than 1 mg/filter, whereby the hollow fibre membrane according to exemplary embodiments of the invention thus also meets strict requirements in relation to elutable PVP.

Customary acceptable elutable PVP quantities of less than 5 mg are acceptable, values smaller than 3 mg/filter are preferred, smaller than 2 mg/filter even more preferred, less than 1 mg/filter quite particularly preferred.

The total PVP content of the finished hollow fibre membrane is approx. 3% (percent by weight). The determination was carried out for example via infrared spectroscopy or pyrolysis gas chromatography with nitrogen and sulphur detection.

The invention claimed is:

1. A hollow fiber membrane consisting of two co-extruded layers A and B,
    wherein layer B has a non-woven structure with a mesh size of 0.1 to 10 μm and layer A has a porous structure, and wherein the material of layers A and B in each case is a mixture of polysulfone (PSU) and polyvinylpyrrolidone (PVP),
    wherein the elutable portion of free residual polyvinylpyrrolidone in the finished membrane is less than 5 mg/0.6-m² membrane surface, and wherein layer A comprises three zones A1, A2, A3 of different porosity, and zone A1 forms the surface of layers A and has pores with average pore size of 0.7-2 μm.

2. The hollow fiber membrane according to claim 1, wherein the internal diameter of the hollow fiber membrane is 280 to 400 μm.

3. The hollow fiber membrane according to claim 1, wherein the total wall width of the hollow fiber membrane is 40 to 80 μm.

4. The hollow fiber membrane according to claim 1, wherein the ratio of the layer thicknesses of layer A to layer B lies in the range of 4:1 to 6:1.

5. The hollow fiber membrane according to claim 1, wherein zone A3 is adjacent to layer B and has a pore-size gradient towards layer B, wherein the pore size increases towards layer B.

6. The hollow fiber membrane according to claim 1, wherein the LDL screening coefficient of the hollow fiber membrane is greater than 0.9.

7. A method for the production of a hollow fiber membrane according to claim 1, comprising the steps of:
    (a) preparing two spinning mass polymer solutions A and B, wherein the viscosity of spinning mass polymer solution A is higher than the viscosity of spinning mass polymer solution B;
    (b) setting the precipitation bath temperature at >70° C.;
    (c) bringing the two spinning mass polymer solutions A and B into contact with an internal precipitant by coextrusion through a hollow fiber spinneret; and
    (d) precipitating said hollow fiber membrane; and
    (e) rinsing and drying said hollow fiber membrane,
    wherein spinning mass polymer solutions A and B each contain a mixture of polysulfone (PSU) and polyvinylpyrrolidone (PVP), the viscosity of spinning mass polymer solution A lies in the range of 7000 to 18000 mPas, and the viscosity of spinning mass polymer solution B is less than 1000 mPas,
    to obtain said hollow fiber membrane in which the elutable portion of free residual polyvinylpyrrolidone in the finished membrane is less than 5 mg/0.6-m² membrane surface.

8. The method according to claim 7, wherein the spinning speed is 200 to 400 mm/s.

9. The method according to claim 8, wherein the spinning block temperature is set to 50 to 90° C.

10. The method according to claim 9, wherein the precipitant is a mixture of dimethylacetamide and water.

11. The method according to claim 7, wherein the viscosity of spinning mass polymer solution A lies in the range of 9000 to 14000 mPas, and the viscosity of spinning mass polymer solution B is less than 1000 mPas and not less than 300 mPas.

12. The method according to claim 7, wherein the viscosity of spinning mass polymer solution A lies in the range of 9000 to 14000 mPas.

13. The method according to claim 12, wherein spinning mass polymer solution A contains 17.5-22.5% polysulfone, 5-8% polyvinylpyrrolidone, and the remainder being solvent.

14. The method according to claim 7, wherein spinning mass polymer solution A contains 15 to 25% polysulfone, 4 to 8% polyvinylpyrrolidone and 81-67% solvent.

15. The method according to claim 7, wherein the viscosity of spinning mass polymer solution B is not less than 300 mPas.

16. The method according to claim 7, wherein spinning mass polymer solution B contains 5 to 15% polysulfone, 4 to 8% polyvinylpyrrolidone, and the remainder being solvent.

17. The method according to claim 7, wherein spinning mass polymer solution B contains 7-13% polysulfone, 4-7% polyvinylpyrrolidone, and the remainder being solvent.

18. The method according to claim 7, wherein spinning mass polymer solution B contains 8-12% polysulfone, 5-7% polyvinylpyrrolidone, and the remainder being solvent.

19. A method according to claim 7, wherein spinning mass polymer solution A contains 15 to 35% polysulfone, 4 to 8% polyvinylpyrrolidone, and the remainder being precipitant.

20. The method according to claim 7, wherein the viscosity of spinning mass polymer solution A lies in the range of 8000 to 15000 mPas.

21. The method according to claim 20, wherein spinning mass polymer solution A contains 15 to 35% polysulfone, 4 to 8% polyvinylpyrrolidone, and the remainder being precipitant.

22. The method according to claim 21, wherein spinning mass polymer solution B contains 8 to 14% polysulfone, 3 to 6% polyvinylpyrrolidone, and the remainder being solvent.

23. A process for subjecting a liquid to nanofiltration or ultrafiltration comprising contacting said liquid with a hollow fiber membrane according to claim 1.

24. A process for subjecting a liquid to hemodialysis, hemodiafiltration, plasmapheresis, or hemofiltration comprising contacting said liquid with a hollow fiber membrane according to claim 1.

25. The hollow fiber membrane according to claim 1, wherein the total wall width of the hollow fiber membrane is 40 to 80 μm and the ratio of the layer thicknesses of layer A to layer B lies in the range of 4:1 to 6:1.

26. The hollow fiber membrane according to claim 25, wherein the ratio of the layer thicknesses of layer A to layer B lies in the range of 4:1 to 6:1.

27. The hollow fiber membrane according to claim 1, wherein layer B is obtained from a spinning mass polymer solution B, and the viscosity of spinning mass polymer solution B is less than 1000 mPas.

28. A hollow fiber membrane according to claim 1, wherein layers A and B are obtained from spinning mass polymer solutions A and B, respectively, and spinning mass polymer solution A has a higher viscosity than the viscosity of spinning mass polymer solution B, and
wherein the viscosity of spinning mass polymer solution A lies in the range of 7000 to 18000 mPas.

29. The hollow fiber membrane according to claim 1, wherein layer A is obtained by extrusion of a spinning mass polymer solution A having a viscosity in the range of 8000 to 15000 mPas.

30. The hollow fiber membrane according to claim 29, wherein spinning mass polymer solution A contains 15 to 35% polysulfone, 4 to 8% polyvinylpyrrolidone, and the remainder being precipitant.

31. The hollow fiber membrane according to claim 1, wherein layers A and B are obtained from spinning mass polymer solutions A and B, respectively, and spinning mass polymer solution A has a higher viscosity than the viscosity of spinning mass polymer solution B.

32. The hollow fiber membrane according to claim 1, wherein the mesh size of layer B is greater than the pore size of all the pores in layer A.

33. A hollow fiber membrane consisting of two co-extruded layers A and B,
wherein layer B has a non-woven structure with a mesh size of 0.1 to 10 μm and layer A has a porous structure, and wherein the material of layers A and B in each case is a mixture of polysulfone (PSU) and polyvinylpyrrolidone (PVP),
wherein layer A comprising 3 zones A1, A2, A3 of different porosity, zone A2 is arranged between zones A1 and A3 and has the smallest average pore diameter of the membrane,
wherein zone A3 is adjacent to layer B and has a pore-size gradient towards layer B, wherein the pore size increases towards layer B,
wherein the mesh size of layer B is greater than the pore size of all the pores in layer A, and
wherein the elutable portion of free residual polyvinylpyrrolidone in the finished membrane is less than 5 mg/0.6-$m^2$ membrane surface.

* * * * *